(12) United States Patent
Yokoyama et al.

(10) Patent No.: US 8,390,812 B2
(45) Date of Patent: Mar. 5, 2013

(54) OPTICAL MEASUREMENT CELL

(75) Inventors: Issei Yokoyama, Kyoto (JP); Kimihiko Arimoto, Kyoto (JP)

(73) Assignee: HORIBA, Ltd., Kyoto-shi (JP)

( * ) Notice: Subject to any disclaimer, the term of this patent is extended or adjusted under 35 U.S.C. 154(b) by 157 days.

(21) Appl. No.: 13/153,228

(22) Filed: Jun. 3, 2011

(65) Prior Publication Data

US 2011/0299067 A1 Dec. 8, 2011

(30) Foreign Application Priority Data

Jun. 4, 2010 (JP) ................................. 2010-129147

(51) Int. Cl.
*G01N 21/00* (2006.01)
(52) U.S. Cl. ....................................................... 356/432
(58) Field of Classification Search ................... 356/432
See application file for complete search history.

(56) References Cited

U.S. PATENT DOCUMENTS 7,518,720 B2 * 4/2009 Kolp et al. .................... 356/246

FOREIGN PATENT DOCUMENTS

JP 08-068746 3/1996

* cited by examiner

*Primary Examiner* — Roy M Punnoose
(74) *Attorney, Agent, or Firm* — Alleman Hall McCoy Russell & Tuttle LLP

(57) ABSTRACT

To make it possible to alter a cell length with reduction of a manufacturing cost so that a spacer can be securely positioned at a desired position, a cell includes: a pair of optical windows sandwiching a flow channel; a cell body provided with an accommodating recess and a solution introduction part and a solution deriving part; a pair of light transmitting members in the accommodating recess and forming the pair of optical windows; a spacer defining a distance between the opposing surfaces of the pair of light transmitting members; and a pressing mechanism for pressing the light transmitting members and the spacer toward the bottom surface of the accommodating recess so as to form the flow channel, wherein a positioning recess having a shape corresponding to the spacer is provided on at least one of the opposing surfaces and the spacer is fitted therein.

4 Claims, 10 Drawing Sheets ved flow cell is connected to a chemical solution 15
OPTICAL MEASUREMENT CELL

TECHNICAL FIELD

The present invention generally relates to an optical measurement cell for measuring a concentration of a chemical solution such as hydrofluoric acid (HF) in a manufacturing process of, e.g., a semiconductor and the like, and, in particular, to an optical measurement flow cell having a pair of optical windows sandwiching a flow channel therebetween for flowing a sample solution.

BACKGROUND ART

This type of flow cell is connected to a chemical solution pipe provided in a semiconductor manufacturing apparatus. A measurement light is irradiated to a sample solution through one of the optical windows of the flow cell and a transmitted light emitted from the other of the optical windows is received. Then, a concentration of a prescribed component contained in the sample solution is calculated based on a transmitted light intensity of the sample solution so that the concentration of the chemical solution is controlled.

Regarding the conventional flow cell, as shown in FIG. 10, a plurality of light transmitting members are bonded by welding or molecular bonding, etc., to be integrally molded so as to form a flow channel connecting from a solution introduction port to a solution derivation port inside the flow cell.

However, since a processing cost for the process of bonding by welding or molecular bonding is high, there is a problem that the manufacturing cost thereof becomes high. In particular, in the case where a material (such as, e.g., sapphire) having a corrosion resistance against a chemical solution such as hydrofluoric acid (HF) is used, since a processing cost of the sapphire is expensive in addition that the material per se is expensive, the manufacturing cost further becomes higher. Also, since the light transmitting members are bonded to each other, a cell length of each flow cell is fixed. Therefore, if it is desired to measure a concentration of a solution using a different cell length, it is needed to prepare a different flow cell and there arises a problem that the cost is raised in addition.

In contrast to this, as disclosed in Patent Literature 1, it is considered to assemble a flow cell by sandwiching the light transmitting members instead of bonding the same. Specifically, a pair of light transmitting parts are arranged to be opposed at a predetermined interval and a spacer is interposed between the pair of the light transmitting members in order to define the interval to be a predetermined distance (i.e., cell length), and a frame body including these parts thereon is sandwiched by a pair of cover plates and screwed to be connected. Thus, the length of the spacer can be set so as to determine the cell length.

However, the spacer sandwiched by the pair of light transmitting members may be displaced by a vibration or shock at a time of carrying or installing the flow cell, or due to a pressure, etc., of a sample solution at a time of measurement, and this may result in the flow channel changing in shape, or the spacer may enter an improper position such as a location on an optical path of the measurement light, and there may occur a problem of measurement error.

In addition, in the assembling process of the flow cell, when the spacer is interposed between the light transmitting members, it is difficult to determine where the spacer is positioned with respect to the light transmitting members, and further when the spacer is disposed and sandwiched between the pair of light transmitting members to be fixed, the spacer may be suffer from the problem of being undesirably misaligned. Therefore, it is difficult to assemble the spacer and it is difficult to form the flow channel in a desired shape.

CITATION LIST

Patent Literature

Patent Literature 1: JP-1996-68746 A

SUMMARY OF INVENTION

Technical Problem

Therefore, the present invention has been made to solve the above problems, and an essential object thereof is to provide an optical measurement cell capable of altering a cell length and ensuring a positioning of a spacer to a desired position while reducing a manufacturing cost.

Solution to Problem

Accordingly, an optical measurement cell pertaining to the present invention has a pair of optical windows sandwiching a flow channel accommodating a sample solution. The cell includes a cell body provided with an accommodating recess having a through hole formed in a part of a bottom surface thereof, a solution introduction part and a solution deriving part which are communicating with an inner circumferential surface of the accommodating recess; a pair of light transmitting members accommodated in the accommodating recess and forming the pair of optical windows; a spacer contacting respective opposing surfaces of the pair of light transmitting members and defining a distance between the opposing surfaces; and a pressing mechanism for pressing the pair of light transmitting members and the spacer toward the bottom surface of the accommodating recess to be brought into close contact with each other so as to form the flow channel connecting to the solution introduction part and the solution deriving part between the pair of light transmitting members, wherein a pair of positioning recesses, each having a shape corresponding to the spacer, are provided on at least one opposing surface of the pair of light transmitting members, the spacer positioned to fit in the positioning recesses so as to be positioned substantially. It is noted here that the terms "to be positioned substantially" means not only that the spacer is fitted to the positioning recess without backlash but also includes a meaning that the spacer is positioned in the positioning recess even with a slight backlash within a range such that no trouble is caused in measurement.

With this arrangement, since each of the light transmitting members and the spacer are pressed and brought into close contact with each other by the pressing mechanism, it is not necessary to execute a costly bonding process so that a manufacturing cost can be reduced. Further, since the light transmitting members are pressed to be brought into close contact with each other by the pressing mechanism without bonding each of the light transmitting members and the spacer, the spacer can be changed to another spacer having different thickness and shape, etc., and thus the cell length can be altered. Further, since the positioning recesses are formed in the light transmitting member, the spacer can be fitted to the positioning recesses so that the spacer can be prevented from being displaced by an external vibration, impact, pressure of the sample solution, etc., with respect to the light transmitting member provided with the positioning recesses. Moreover, the spacer can be securely positioned in a desired position so that the flow channel can be formed to have a desired shape. In addition, since the positioning recesses can be formed by cutting or polishing, etc., there is no need to separately attach an additional positioning member by bonding, and hence the manufacturing cost can be also reduced.

Each positioning recess is preferably provided in an outer edge portion of the opposing surface, and the bottom surface of the positioning recess is formed in a stepwise shape leading to a side surface of the light transmitting member, and the spacer is sandwiched between the inner circumferential surface of the accommodating recess and the side surface of the positioning recess facing the inner circumferential surface so as to be positioned. With this arrangement, the flow channel can be formed in a central portion of the cell. Further, since the positioning recess is provided in the outer edge portion, it is more easily formed by polishing than the case of providing the positioning recess at a central portion of the opposing surfaces.

In the assembling process, in order to securely position the spacer by confirming the position of the positioning recess of the light transmitting member previously arranged, it is desirable that the positioning recesses are provided on the opposing surfaces of the light transmitting members arranged in a bottom surface side of the accommodating recess.

It is preferable that the accommodating recess has substantially a circular shape in plan view, and each of the pair of light transmitting members has substantially a circular shape in plan view fitted to the accommodating recess, and the spacer is a pair of partial arc plates each having a side surface of a partial arc shape of substantially the same circle of the pair of light transmitting members in plan view, and the positioning recesses are provided to have a shape substantially the same as the spacer in plan view and are formed in the outer edge portions of the opposing surfaces and sandwich the solution introduction part and the solution deriving part. With this arrangement, since each member is mainly formed in a circular shape, a processing is easy and a manufacturing cost can be reduced. Also, there is an advantage that sealing can be easily carried out by a seal member such as an O ring. Moreover, in the case where a pair of members is used as the spacer, a contact pressure applied to the members can be more reduced than the case where any one of the pair of members is used as the spacer, and therefore breakage of the spacer can be prevented.

Advantageous Effects of Invention

According to the present invention constructed as mentioned above, it becomes possible to alter the cell length while reducing the manufacturing cost and the spacer can be securely positioned at a desired position.

DESCRIPTION OF EMBODIMENTS

Figure 1:
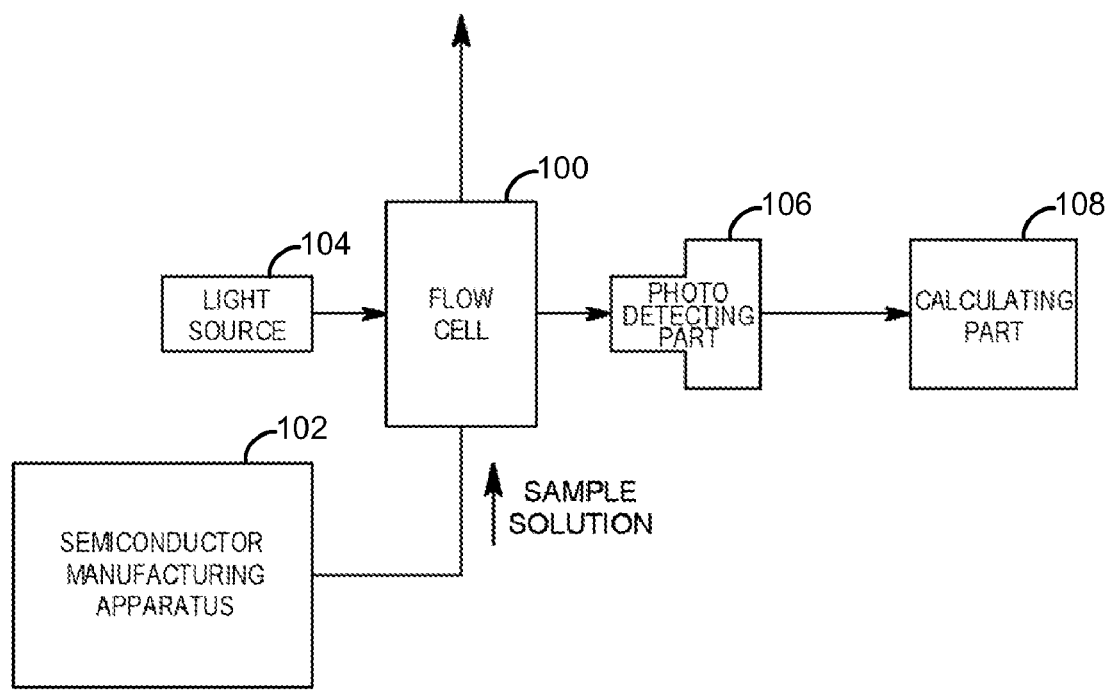
FIG. 1 is a schematic view using an optical measurement flow cell in an embodiment of the present invention.

The following describes an optical measurement flow cell 100 pertaining to an embodiment of the present invention referring to the accompanying drawings.

As shown in FIGS. 1-5, the optical measurement flow cell 100 pertaining to the present embodiment is connected to a pipe L provided in a semiconductor manufacturing apparatus 102 and it is used for measuring a concentration of a chemical solution (sample solution) such as hydrofluoric acid. The flow cell 100 includes a pair of optical windows 23 which are facing each other and sandwiching a flow channel in which the sample solution flows. The sample solution is irradiated with light emitted by a light source 104 through one of the optical windows 23, and a transmitted light outputted through the other optical window 23 is received by a photo detecting part 106. A calculating part 108 receives a light intensity signal from the photo detecting part 106 so that a concentration of a prescribed component contained in the sample solution is calculated by the calculating part 108 based on the light intensity signal. With use of the concentration obtained in this manner, the concentration of the chemical solution is controlled.

Specifically, as shown in FIGS. 2 to 5, the optical measurement flow cell 100 includes a flow cell body 10, a pair of light transmitting members 20 and 21, a spacer 30 and a pressing mechanism 80.

Figure 2:
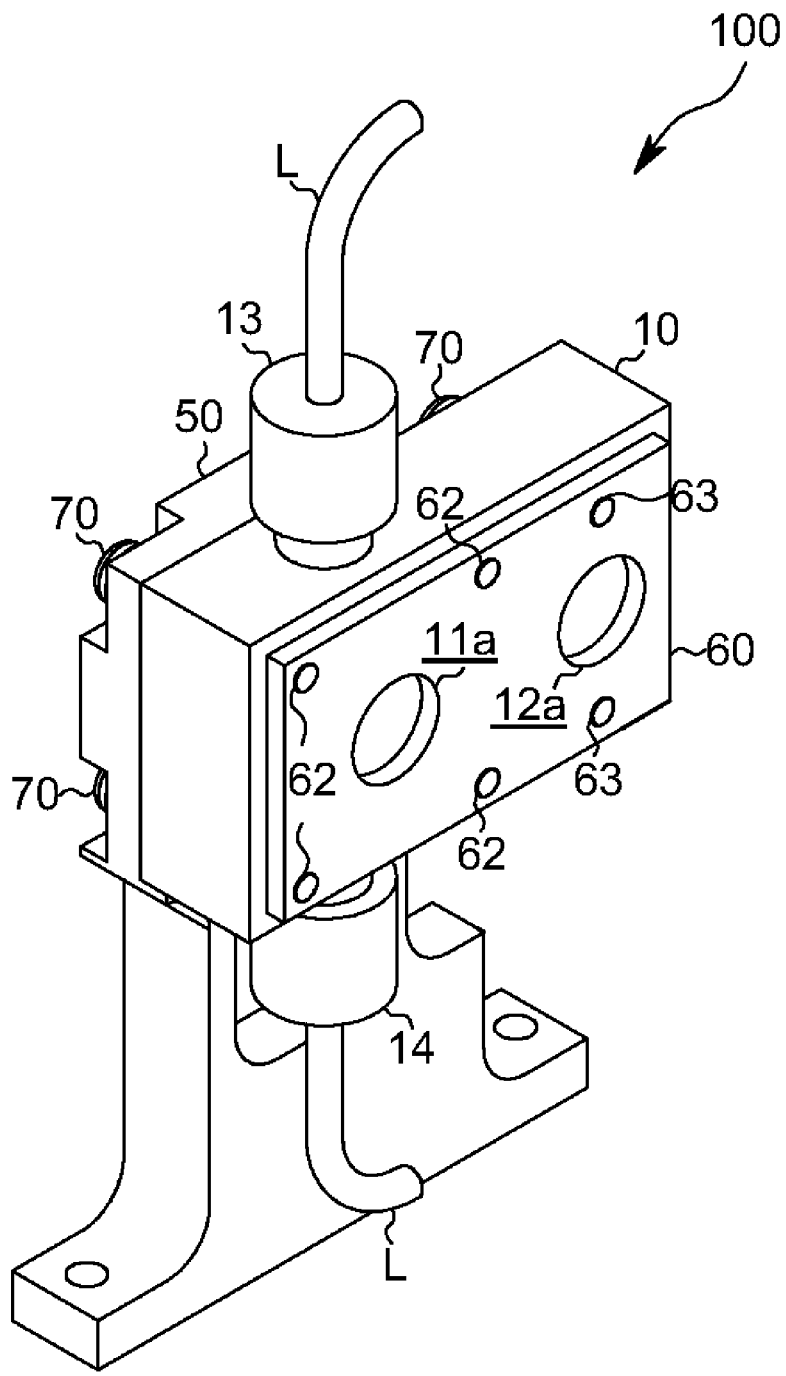
FIG. 2 is a perspective view showing the optical measurement flow cell in the same embodiment.

The flow cell body 10 has a generally rectangular parallel piped shape as shown in FIG. 2, and it includes an accommodating recess 11 formed in the front face thereof, a solution deriving part 13 and a solution introduction part 14 which communicate with an inner circumferential surface 11c of the accommodating recess 11. The flow cell body 10 is formed by using, e.g., PTFE (polytetrafluoroethylene). In order to prevent air bubbles from remaining in the cell, the sample solution is introduced from the solution introduction part 14 provided in a lower position and is derived from the solution deriving part 13 provided in an upper position.

Figure 3:
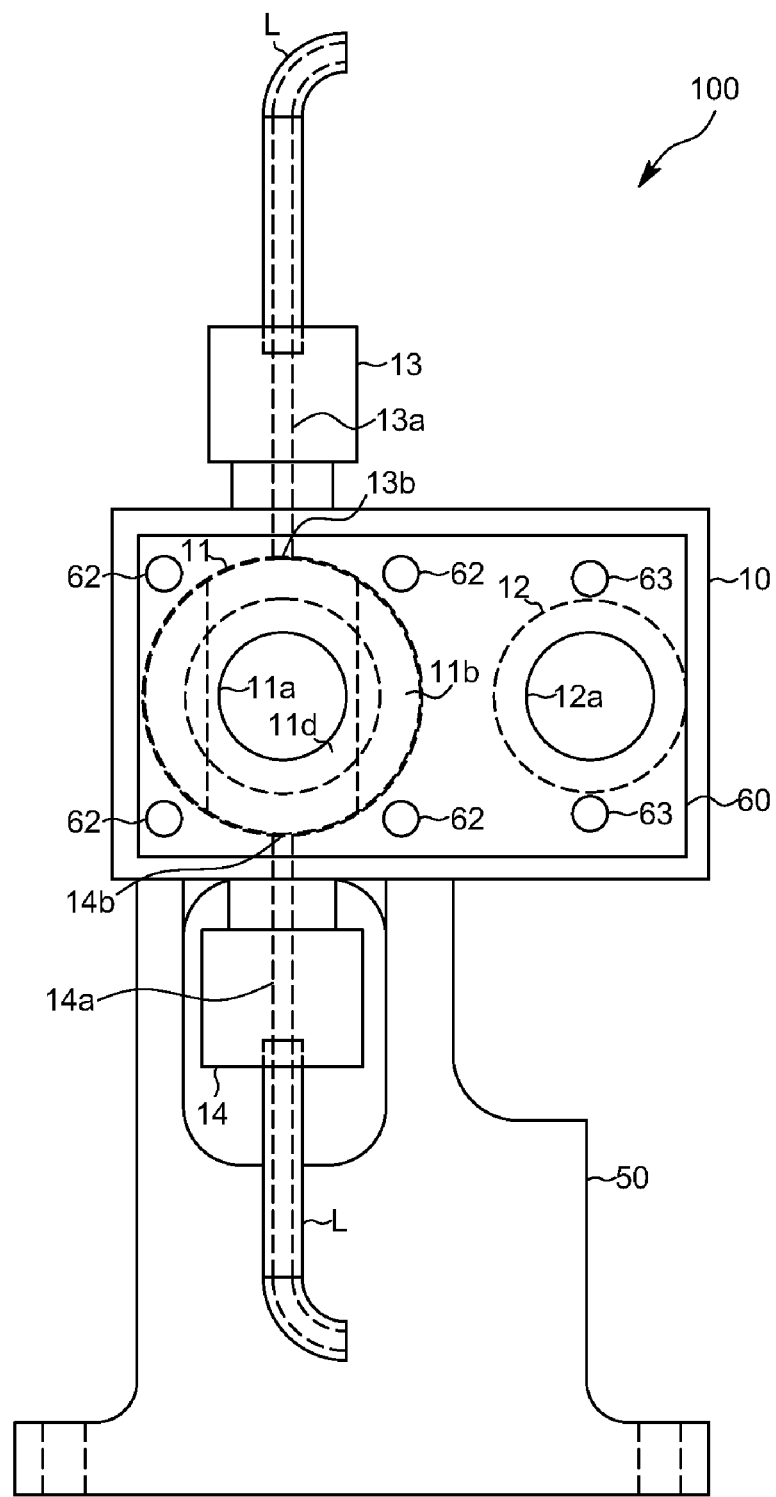
FIG. 3 is a back view of the optical measurement flow cell in the same embodiment.

The accommodating recess 11 is intended to accommodate the pair of light transmitting members 20 and 21 and the spacer 30 inside thereof. As shown in FIG. 3, the accommodating recess 11 has a generally cylindrical shape (approximately circular in plan view), and a through hole 11a for passing light is formed in a center portion of the bottom surface 11d thereof and an annular groove 11b is formed in an outer periphery of the bottom surface 11d. The accommodating recess 11, the thorough hole 11a, and the annular groove 11b are formed concentrically in the plan view.

Figure 4:
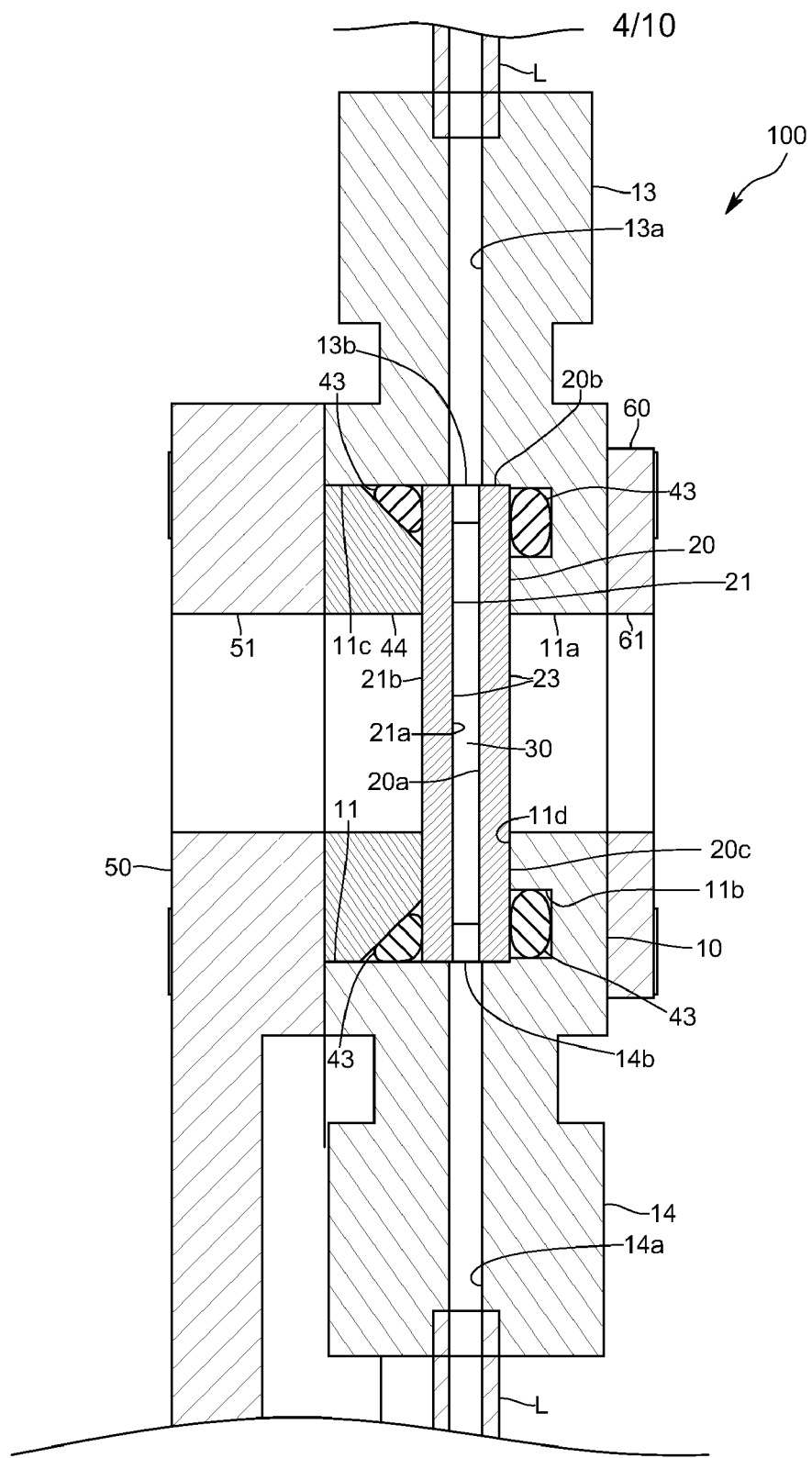
FIG. 4 is a partially enlarged longitudinal section view of the optical measurement flow cell in the same embodiment.

The solution deriving part 13 is intended to derive the sample solution from the accommodating recess 11. As shown in FIG. 4, the solution deriving part 13 includes an internal flow channel 13a having one end thereof opened to an upper portion of the inner circumferential surface 11c of the accommodating recess 11 and the other end thereof connected to an external pipe L. The internal flow channel 13a of the solution deriving part 13 is formed to be perpendicular to the upper and lower surfaces of the flow cell body 10 and is formed in a straight line passing through the center of the generally circular accommodating recess 11. Further, an upper portion of the solution deriving part 13 has a function as a joint.

The solution introduction part 14 is intended to introduce a sample solution to the accommodating recess 11. As shown in FIG. 4, the solution introduction part 14 includes an internal flow channel 14a having one end thereof opened to a lower portion of the inner circumferential surface 11c of the accommodating recess 11 and the other end thereof connected to an external pipe L. The internal flow channel 14a of the solution introduction part 14 is formed to be perpendicular to the upper and lower surfaces of the flow cell body 10 and is formed in a straight line passing through the center of the generally circular accommodating recess 11. Further, a lower portion of the solution introduction part 14 has a function as a joint. Further, the opening 13b of the solution deriving part 13 and the opening 14b of the solution introduction part 14 are opposed to each other across the center of the generally circular accommodating recess 11.

Figure 5:
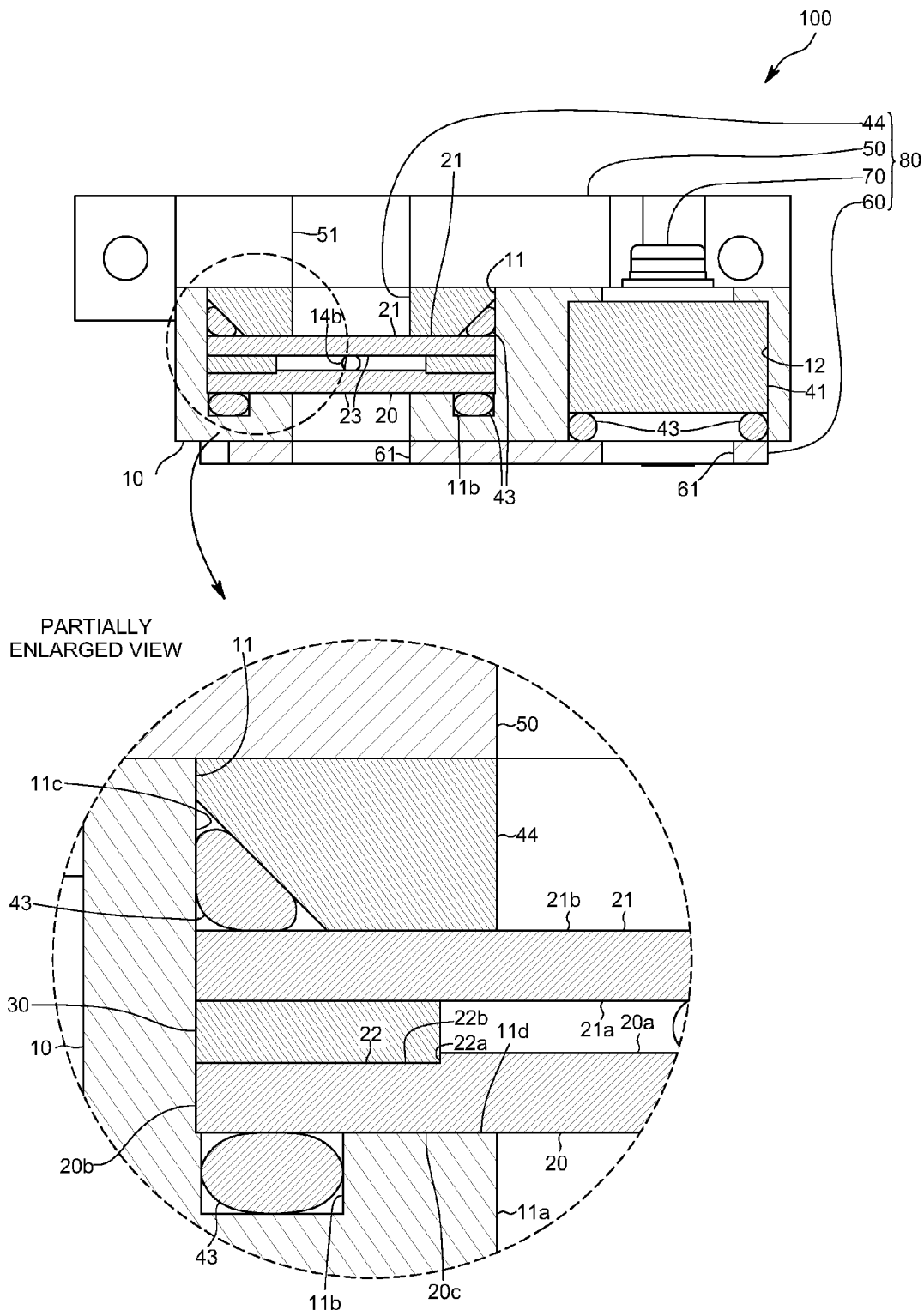
FIG. 5 is an enlarged lateral section view of the optical measurement flow cell in the same embodiment.
Figure 6:
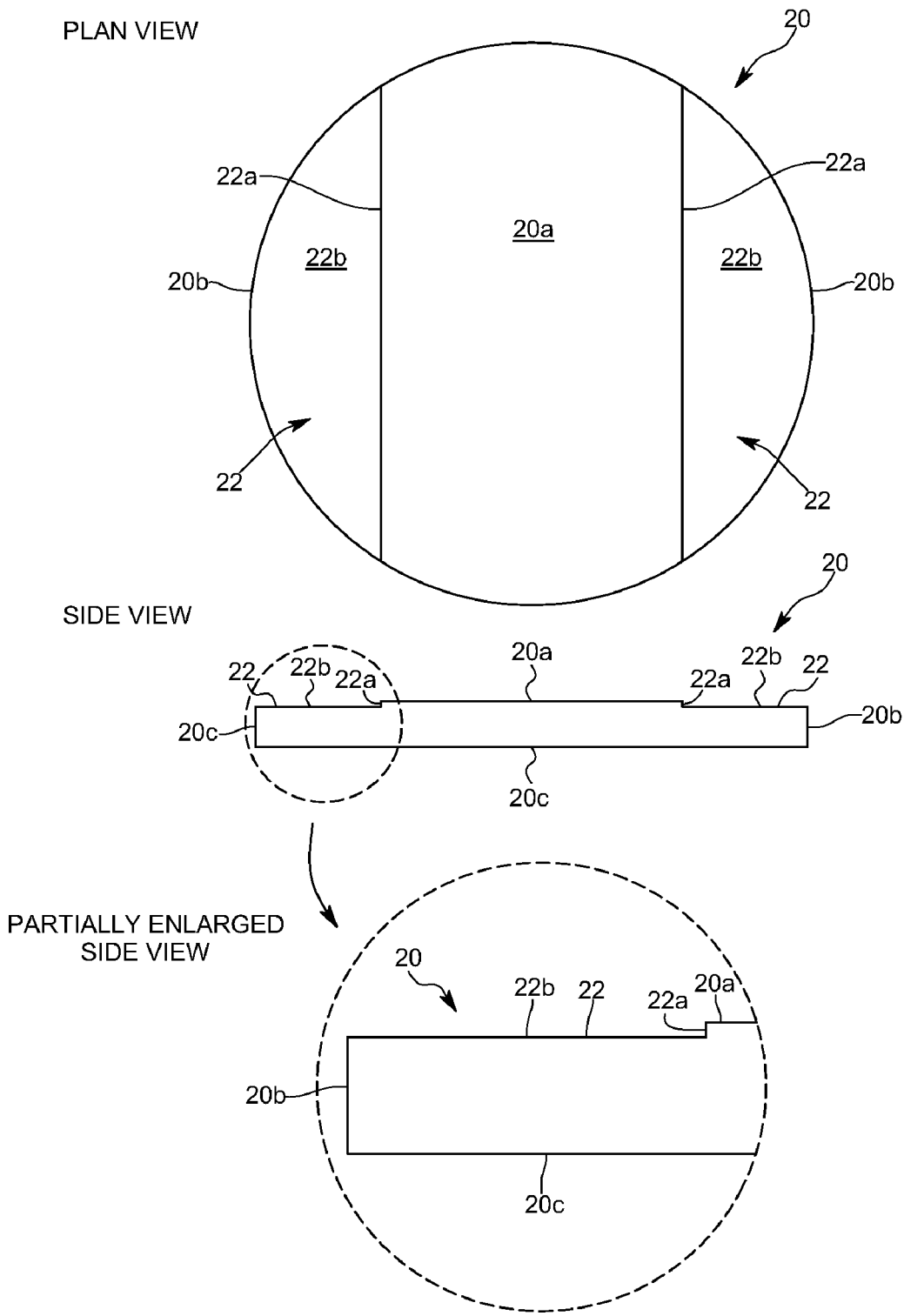
FIG. 6 is a diagram showing a light transmitting member having an accommodation recess formed therein in the same embodiment.

As shown in FIGS. 4 and 5, the pair of light transmitting members 20 and 21 are accommodated in the accommodating recess 11 and opposed to each other by a space with a predetermined distance to form the pair of optical windows 23 of the flow cell 100. The pair of light transmitting members 20 and 21 includes a first light transmitting member 20 accommodated in a side of the bottom surface 11d of the accommodating recess 11 and a second light transmitting member 21 accommodated in a side of the opened face of the accommodating recess 11. The first light transmitting member 20 and the second light transmitting member 21 are formed substantially in the same shape in plan view, and each of them is substantially disc-shaped to be fitted to the accommodating recess 11 as shown in FIG. 6. In a state that each of the light transmitting members 20 and 21 is accommodated in the accommodating recess 11, as shown in FIGS. 4 and 5, a lower surface 20c of the first light transmitting member 20 (i.e., a surface in an opposite side of an opposing surface 20a) is in contact with the bottom surface 11d of the accommodating recess 11, and the opposing surface 20a of the first light transmitting member 20 and the opposing surface 21a of the second light transmitting member 21 are respectively in parallel to the bottom surface 11d of the accommodating recess 11.

Referring to a thickness of the first light transmitting member 20 in relation to the opening 13b of the solution deriving part 13 and the opening 14b of the solution introduction part 14, as shown in FIG. 4, the thickness is set so as not to block the opening 13b of the solution deriving part 13 and the opening 14b of the solution introduction part 14 by the first light transmitting member 20 in a state that the first light transmitting member 20 is accommodated in the accommodating recess 11. That is, the thickness of the first light transmitting member 20 and the positions, shapes and sizes of the opening 13b of the solution deriving part 13 and the opening 14b of the solution introduction part 14 are relatively set so that the thickness of the first light transmitting member 20 is smaller than a distance from the bottom surface 11d of the accommodating recess 11 to the end in a side of the opening of the accommodating recess 11 in the opening 13b of the solution deriving part 13 and the opening 14b of the solution introduction part 14. Herein, the pair of light transmitting members 20 and 21 is formed by using sapphire that has excellent properties of corrosion resistance against chemicals such as hydrofluoric acid (HF), strength withstanding a pressing, and light transmissibility.

Figure 7:
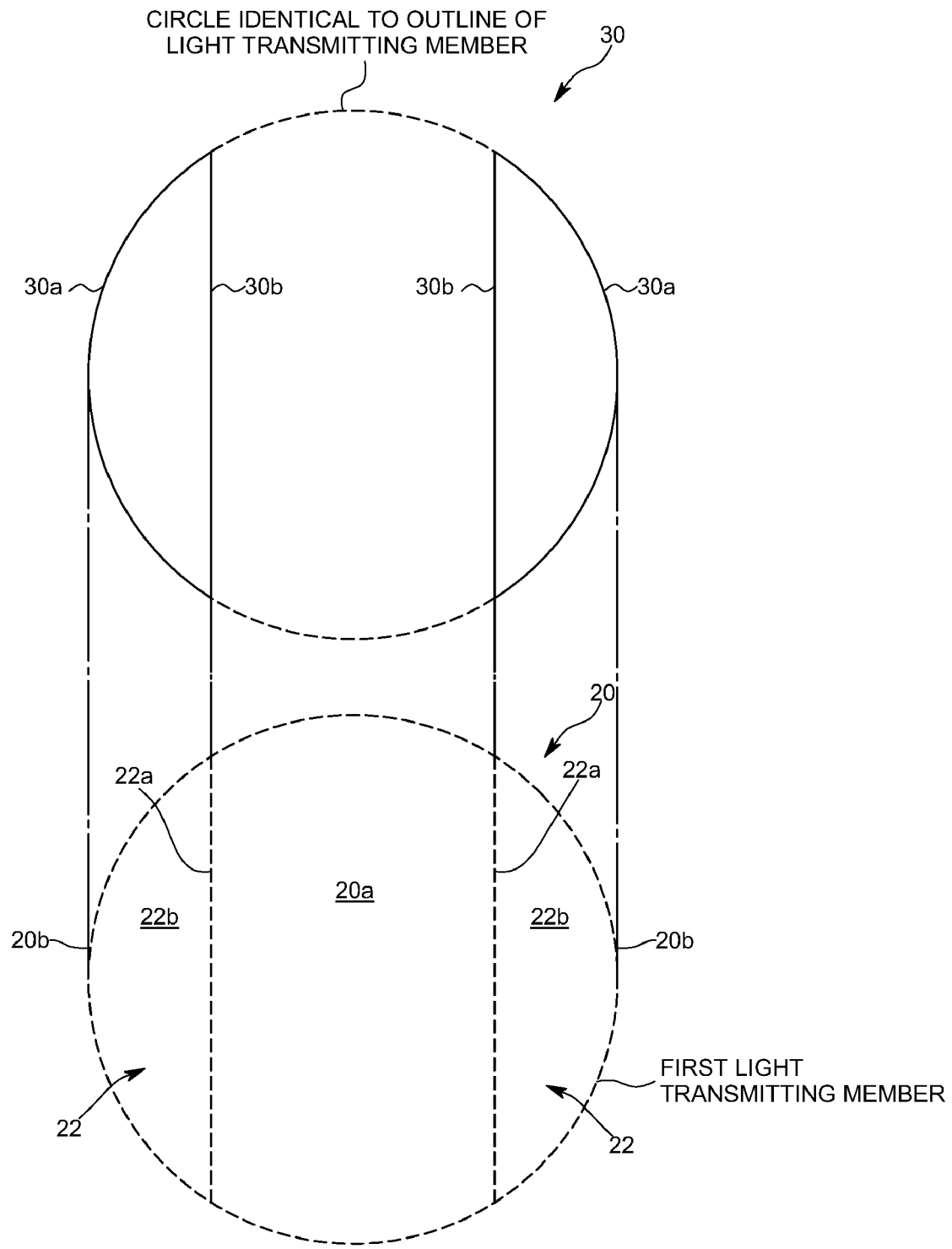
FIG. 7 is a plan view showing a spacer in the same embodiment.

As shown in FIGS. 4 and 5, the spacer 30 is in contact with the opposing surfaces 20a and 21a of the pair of light transmitting members 20 and 21, respectively, so that the opposing surfaces 20a and 21a are arranged in parallel to each other so as to determine the distance between the opposing surfaces 20a and 21a of the pair of light transmitting members 20 and 21. In addition, as shown in FIG. 7, the spacer 30 is formed of a pair of partially arc-shaped plates having the same shape as each other. Each of the pair of partially arc-shaped plates is formed of a curved outer surface 30a and a straight inner surface 30b. The outer surface 30a is partially arc-shaped of the substantially same circle as the pair of light transmitting members 20 and 21 (substantially same circle of the accommodating recess 11) in plan view. The spacer 30 is formed by using sapphire which has excellent properties of corrosion resistance against chemical solutions such as hydrofluoric acid (HF) and strength withstanding a pressing.

Figure 8:
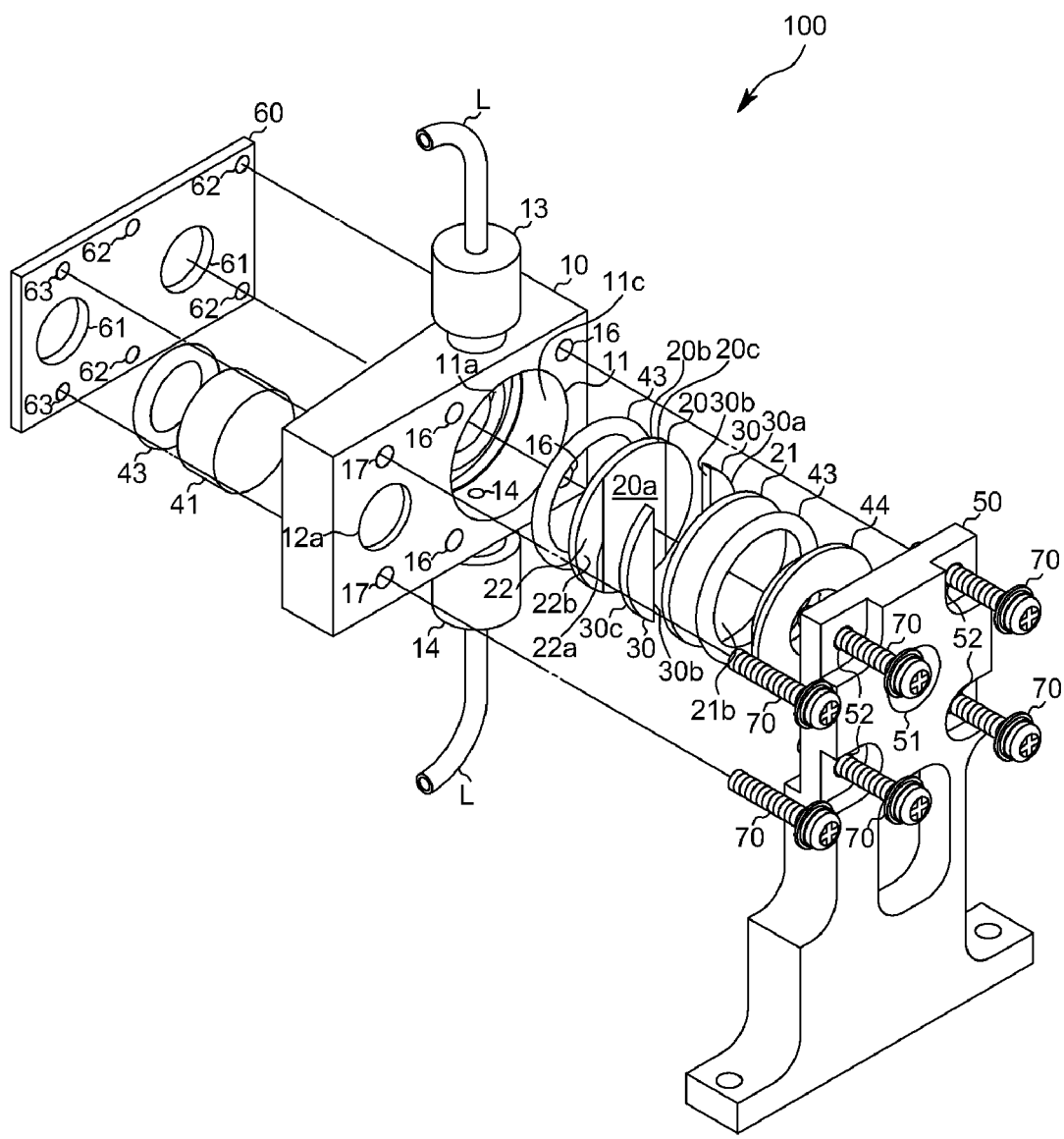
FIG. 8 is an exploded perspective view showing the optical measurement flow cell in the same embodiment.

As shown in FIGS. 3 to 5, the pressing mechanism 80 is adapted to press the first light transmitting member 20, the spacer 30 and the second light transmitting member 21 placed in sequence from the bottom surface 11d of the accommodating recess 11 to be brought into close contact toward the bottom surface 11d of the accommodating recess 11 so as to form a flow channel between the pair of light transmitting members 20 and 21 and the spacer 30 to be communicated with the solution deriving part 13 and the solution introduction part 14. The pressing mechanism 80 includes a first holding plate 50 and a second holding plate 60 for sandwiching the flow cell body 10 therebetween, an inclined ring 44 interposed between the first holding plate 50 and the second light transmitting member 21 and connecting members 70 such as, e.g., bolts for connecting each of the holding plates. Through holes 16 (four in this example) for inserting the connecting members 70 are penetrating from the front to the back around the accommodating recess 11 of the flow cell body 10, as shown in FIG. 8.

As shown in FIGS. 3 to 5 and FIG. 8, the first holding plate 50 is attached to the front side of the flow cell body 10 so as to restrain each of the members accommodated in the accommodating recess 11. A through hole 51 for passing through the light and insertion through holes 52 (four in this example) for inserting the connecting members 70 to be passed are provided in a top portion of the first holding plate 50. The through hole 51 is provided at a position corresponding to the through hole 11a of the accommodating recess 11. Each of the insertion through holes 52 is provided at a position corresponding to the insertion through hole 16 of the flow cell body 10. In addition, holes for attaching the flow cell 100 to an external device, etc., are provided in the bottom portion of the first holding plate 50.

As shown in FIGS. 3 to 5, the second holding plate 60 is attached to the back surface side of the flow cell body 10 and it is a substantially rectangular plate of a size smaller than the back surface of the flow cell body 10. Moreover, a through hole 61 for passing light and female screw holes 62 (four in this example) for screwing the connecting members 70 are provided in the second holding plate 60. The through hole 61 is provided at a position corresponding to the through hole 11a of the accommodating recess 11. The female screw holes 62 are provided at positions corresponding to the insertion through holes 16 of the flow cell body 10, respectively.

As shown in FIGS. 4 and 5, the inclined ring 44 is respectively in contact with the first holding plate 50 and the second light transmitting member 21 so as to transfer a pressing force to the first holding plate 50 and the second light transmitting member 21. Specifically, the inclined ring 44 has a generally cylindrical shape and its outer peripheral surface and bottom surface contacting the second light transmitting member 21 are partially cut off in a slanting direction so as to form a tapered slope surface. The inner diameter of the inclined ring 44 is substantially coincident with a diameter of the through hole 11a of the accommodating recess 11. Further, the thickness of the inclined ring 44 is determined in such a manner so that the total height of the first light transmitting member 20, the spacer 30, the second the light transmitting member 21, and the inclined ring 44 accommodated in sequence in the accommodating recess 11 is larger than the depth of the accommodating recess 11. That is, the thickness of the inclined ring 44 is determined so that a part of the inclined ring 44 protrudes from the accommodating recess 11.

Further, as shown in FIGS. 4 and 5, a seal member such as an O ring 43 is provided between a slope surface of the inclined ring 44 and the top surface 21b of the second light transmitting member 21 (the surface in the opposite side of the opposing surface 21a) and the inner circumferential surface 11c of the accommodating recess 11. When the inclined ring 44 is pressed toward the bottom surface 11d of the accommodating recess 11, the O ring 43 is compressed. In this state, the O ring 43 and the top surface 21b of the second light transmitting member 21 are air-tightly brought into close contact with each other. In the meanwhile, the O ring 43 and the inner circumferential surface 11c of the accommodating recess 11 are air-tightly brought into close contact with each other. As a result, even in the case where the sample solution flowing through the flow channel leaks out from a clearance between each of the light transmitting members 20 and 21 and the spacer 30 to the inner circumferential surface 11c of the accommodating recess 11, the solution leakage to the outside can be prevented. Note here that the O ring 43 is formed by using PTFE (polytetrafluoroethylene).

As shown in FIGS. 5 and 6, a positioning recess 22 having a shape corresponding to the spacer 30 is provided on at least one of the opposing surfaces 20a and 21a of the pair of light transmitting members 20 and 21 (herein, the opposing surface 20a of the first light transmitting member 20). The positioning recess 22 is intended to fit the spacer 30 to effect an approximate positioning. Specifically, a pair of positioning recesses 22 is respectively provided at both ends of the outer periphery of the opposing surface 20a in a manner of sandwiching the solution deriving part 13 and the solution introduction part 14 under the condition that the first light transmitting member 20 is accommodated in the accommodating recess 11. A bottom surface 22b of the positioning recess 22 is formed in a stepwise shape that is connected to the side surface 20b of the light transmitting member. In other words, the positioning recesses 22 are respectively formed in a stage lower by one step toward the radial direction from a pair of parallel chords with respect to the outer periphery of the first light transmitting member 20.

As shown in FIG. 7, in a state that the spacer 30 is fitted into the positioning recess 22, the curved outer surface 30a of the spacer 30 and the side surface 20b of the first light transmitting member 20 are coincided with each other in plan view, and as shown in FIG. 5, a straight inner surface 30b of the spacer 30 is in contact with the side surface 22a of the positioning recess 22. Further, as shown in FIG. 5, the side surfaces 22a of the positioning recess 22 are provided substantially in parallel with each other and a distance between the side surfaces 22a is defined to be larger than the diameter of the through hole 11a formed in the accommodating recess 11 and also to be larger than each of the widths of the opening 13b of the solution deriving part 13 and the opening 14b of the solution introduction part 14, respectively. The depth of the positioning recess 22 can be appropriately set and is set to about 0.1 mm in the present embodiment. Further, the spacer 30 defines a distance (cell length) between the opposing surfaces 20a and 21a and the distance is calculated by subtracting the depth of the positioning recess 22 from the thickness of the spacer 30.

As shown in FIG. 5, in a state that the pair of light transmitting members 20 and 21 and the spacer 30 are accommodated in the accommodating recess 11, the spacer 30 is sandwiched between the inner circumferential surface 11c of the accommodating recess 11 and the side surface 22a of the positioning recess 22 opposing to the inner circumferential surface 11c and it is positioned so as not to be displaced. Further, as shown in FIGS. 5 and 6, the centers of the openings 13b and 14b of the solution deriving and solution introduction parts 13 and 14 are positioned between the opposing surfaces 20a and 21a, and between the inner surfaces 30b and 30b of the spacer 30, and between the side surfaces 22a and 22a of the positioning recess 22.

Further, the flow cell 100 in the present embodiment includes a reference cell in addition to the flow channel (sample cell) in which the sample solution flows. The reference cell is provided for obtaining a reference transmitted light intensity by passing through the light, and as shown in FIG. 5, it mainly includes a reference accommodating recess 12 and a reference column member 41 which are provided in the flow cell body 10.

The reference accommodating recess 12 is intended to accommodate the reference column member 41. As shown in FIG. 3, the reference accommodating recess 12 is provided in a generally circular shape in plan view on the back surface of the flow cell body 10 spaced from the accommodating recess 11 by a predetermined distance. A through hole 12a is formed in a part of a bottom surface of the reference accommodating recess 12. As shown in FIG. 3, the reference accommodating recess 12 and the through hole 12a are formed concentrically in the plan view.

The reference column member 41 is provided for obtaining a reference transmitted light intensity by passing through the light, and it is formed in a generally column shape in plan view to be fitted to the reference accommodating recess 12. The length of the reference column member 41 is appropriately determined in accordance with a refractive index of a given component to be measured. The reference column member 41 is formed by using silica glass.

Further, connecting holes 17 (two in the example shown in FIG. 8) for passing through the connecting member 70 are formed around the reference accommodating recess 12 of the flow cell body 10 to penetrate from the front surface to the back surface. Female screw holes 63 (two in the example shown in FIG. 8) are formed in the position of the second holding plate 60 corresponding to the connecting holes 17 in order for screwing the connecting member 70. Also, a through hole 61 for passing through the light is formed in the position of the second holding plate 60 corresponding to the through hole 12a of the reference accommodating recess 12.

Next, the following describes an example of a procedure of assembling the flow cell 100 of the present embodiment referring to FIG. 8.

First, the assembling of the reference cell is described. The reference column member 41 and the O ring 43 are sequentially accommodated in the reference accommodating recess 12 of the flow cell body 10 with its back surface directed up. Then, the second holding plate 60 is mounted on the opening of the reference accommodating recess 12 (back surface of the flow cell body 10), and the connecting members 70 of bolts are inserted through the connecting holes 17 in a side of the reference accommodating recess 12 of the flow cell body 10 from a front surface side of the flow cell body 10 and further thread-fastened to the female screw holes 63 formed in the second holding plate 60 corresponding to the connecting holes 17. As a result, the second holding plate 60 and the reference column member 41 are attached to the flow cell body 10 so that the reference cell is formed.

Next, the assembling of the flow channel (sample cell) in which the sample solution flows is described. After the assembling of the reference cell mentioned above, the flow cell body 10 is turned upside down with the front surface thereof directed up. Next, as shown in FIGS. 5 and 8, the O ring 43 is accommodated in the annular groove 11b of the accommodating recess 11 in the flow cell body 10, and subsequently the first light transmitting member 20 is accommodated therein. At this time, the positioning recesses 22 are directed to a side of the opening of the accommodating recess 11, i.e., directed to the front side of the flow cell body 10, and the positioning recesses 22 are so arranged as to sandwich the solution deriving part 13 and the solution introduction part 14. Further, the spacer 30 is arranged in a manner that the bottom surface 30c of the spacer 30 is fitted to the positioning recess 22. In this state, since the spacer 30 is sandwiched between the inner circumferential surface 11c of the accommodating recess 11 and the side surface 22a of the positioning recess 22 opposing to the inner circumferential surface 11c, the spacer 30 can be positioned so as not to be displaced with respect to the first light transmitting member 20.

Then, the first holding plate 50 is mounted to the opening of the accommodating recess 11 in which the respective members are accommodated. Subsequently, the connecting members 70 of bolts are inserted through the insertion holes 52 defined in the first holding plate 50 and inserted through the through holes 16 defined in a side of the accommodating recess 11 of the flow cell body 10 from the front side thereof and further thread-fastened to the female screw holes 62 provided in the second holding plate 60. Thus, the first holding plate 50 is attached to the flow cell body 10. When the bolts are further tightened, the pair of light transmitting members 20 and 21 and the spacer 30 are pushed by pressing toward the bottom surface 11d of the accommodating recess 11 to be brought into close contact with each other so that the flow channel connected to the solution deriving part 13 and the solution introduction part 14 is formed between the pair of light transmitting members 20 and 21 and the accommodating recess 11. In this state, the spacer 30 defines a distance (cell length) between the opposing surfaces 20a and 21a and the distance is calculated by subtracting the depth of the positioning recess 22 from the thickness of the spacer 30.

Further, the following describes an example of a procedure in the case of altering the distance (cell length) between the opposing surfaces 20a and 21a of the pair of light transmitting members 20 and 21. First, after the first holding plate 50 is detached, the inclined ring 44, the O ring 43, the second light transmitting member 21, and the spacer 30 are detached. Then, a spacer 30 of a different thickness, second light transmitting member 21, the O ring 43 and the inclined ring 44 are sequentially accommodated, and the first holding plate 50 is reattached. Thus, there is formed a flow channel having a different distance (cell length) between the opposing surfaces 20a and 21a of the pair of light transmitting members 20 and 21.

According to the present embodiment, since each of the light transmitting members 20 and 21 and the spacer 30 are pressed and brought into close contact with each other by the pressing mechanism 80, it is not necessary to execute a costly bonding process so that a manufacturing cost can be reduced. Further, since the light transmitting members are pressed to be brought into close contact with each other by the pressing mechanism 80 without bonding each of the light transmitting members 20 and 21 and the spacer 30, the spacer 30 can be changed to another spacer 30 having different thickness and shape, etc., and thus the cell length can be altered. Further, since the positioning recess 22 is formed in the light transmitting member, the spacer 30 can be fitted to the positioning recess 22 so that the spacer 30 can be prevented from being displaced by an external vibration, impact, pressure of the sample solution, etc., with respect to the light transmitting member provided with the positioning recess 22. Moreover, the spacer 30 can be securely positioned in a desired position so that the flow channel can be formed to have a desired shape. In addition, since the positioning recess 22 can be formed by cutting or polishing, etc., there is no need to separately attach an additional positioning member by bonding, and hence the manufacturing cost can be also reduced.

Further, in a state that the first light transmitting member 20 is accommodated in the accommodating recess 11, since the positioning recess 22 is located outside than the through hole 11a of the accommodating recess 11, the spacer 30 can be kept from entering onto an optical path of the measurement light so that an occurrence of a measurement error can be reduced. Moreover, in a state that the O ring 43 is urged by a pressing force from the first holding plate 50 via the slope surface of the inclined ring 44, the O ring 43 and the top surface 21b of the second light transmitting member 21 are air-tightly brought into close contact with each other and also the O ring 43 and the inner circumferential surface 11c of the accommodating recess 11 are air-tightly brought into close contact with each other, even in the case where the sample solution flowing through the flow channel leaks out from a space between each of the light transmitting members 20 and 21 and the spacer 30 to the inner circumferential surface 11c of the accommodating recess 11, the solution can be prevented from leaking outside.

In addition, in the present embodiment, since the reference cell is configured by using the reference column member 41 including silica glass, the manufacturing cost can be lower than that including sapphire. Also, since the joint is integrally formed with the flow cell body 10, a leakage of solution from a joined portion between the joint and the flow cell body 10 can be prevented.

It is noted that the present invention is not limited to the embodiments described above. For example, in the present embodiment, although the cell length is altered by replacing the spacer with another spacer having a different thickness, the cell length may also be altered by replacing the first light transmitting member with another first light transmitting member having a positioning recess of a different depth.

Further, although the joint for fluid coupling is integrally formed with the flow cell body, the joint may be separately attached to the flow cell body.

Furthermore, in the case where the total height of the O ring, the first light transmitting member, the spacer, the second light transmitting member, and the inclined ring stacked in sequence becomes smaller than the depth of the accommodating recess by altering the thickness of the spacer or the depth of the positioning recess (i.e., the inclined ring and so forth are completely accommodated in the accommodating recess) so that these members cannot be pressed by the first holding plate, it may be sufficient to replace the inclined ring by another inclined ring having a larger thickness. Although the first holding plate and the inclined ring are separately provided, the first holding plate and the inclined ring may be attached by bonding or may be integrally molded.

In addition, although the positioning recess is formed in a stage shape lowered by one step, it may be formed in a stair shape of multi steps and the like. Further, the spacer may be generally crescent shaped or spindle shaped having a side surface of a partially arc shape of a circular substantially identical to a pair of light transmitting members in plan view.

Figure 9:
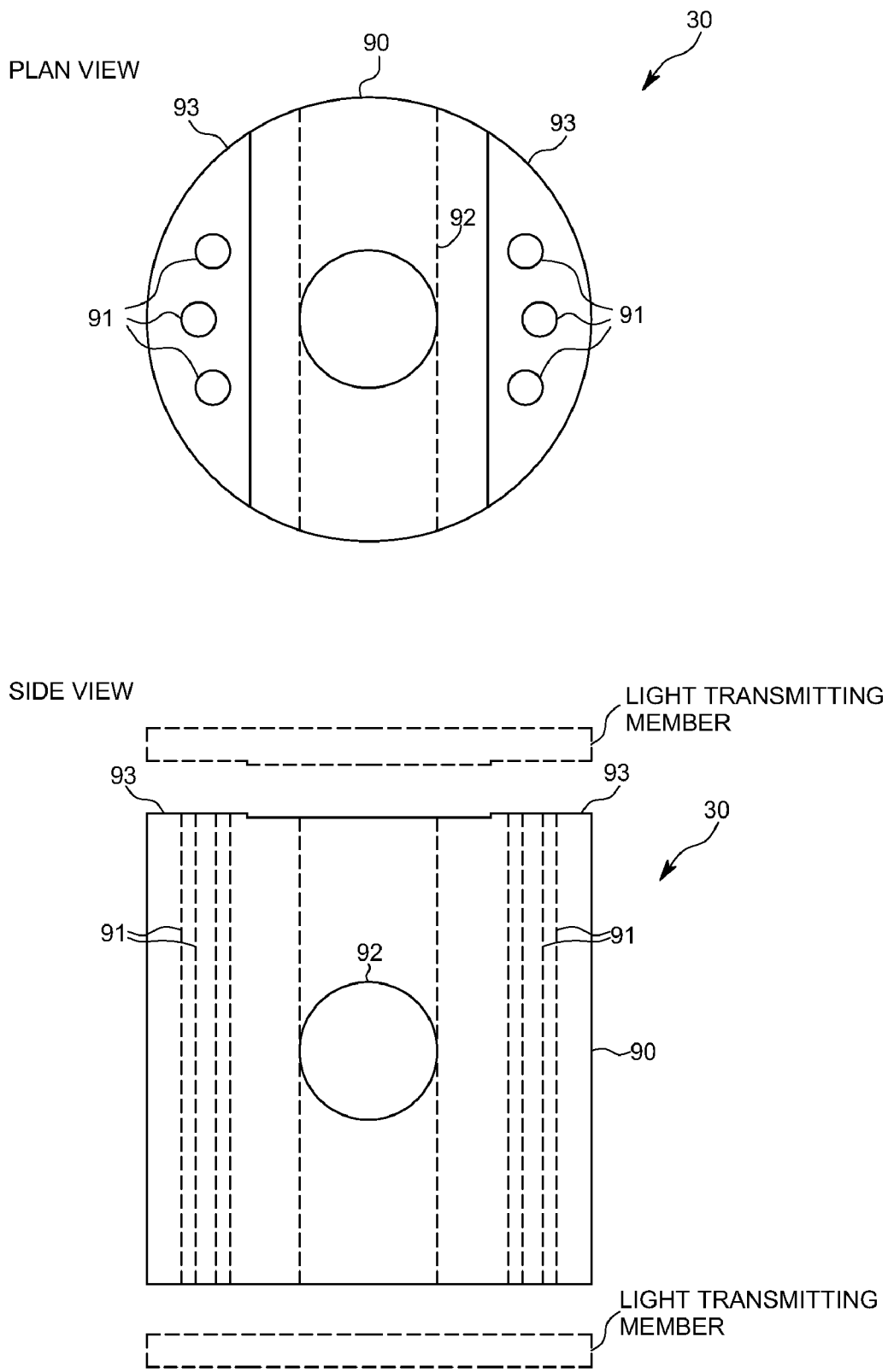
FIG. 9 is a diagram showing a spacer in another embodiment.
Figure 10:
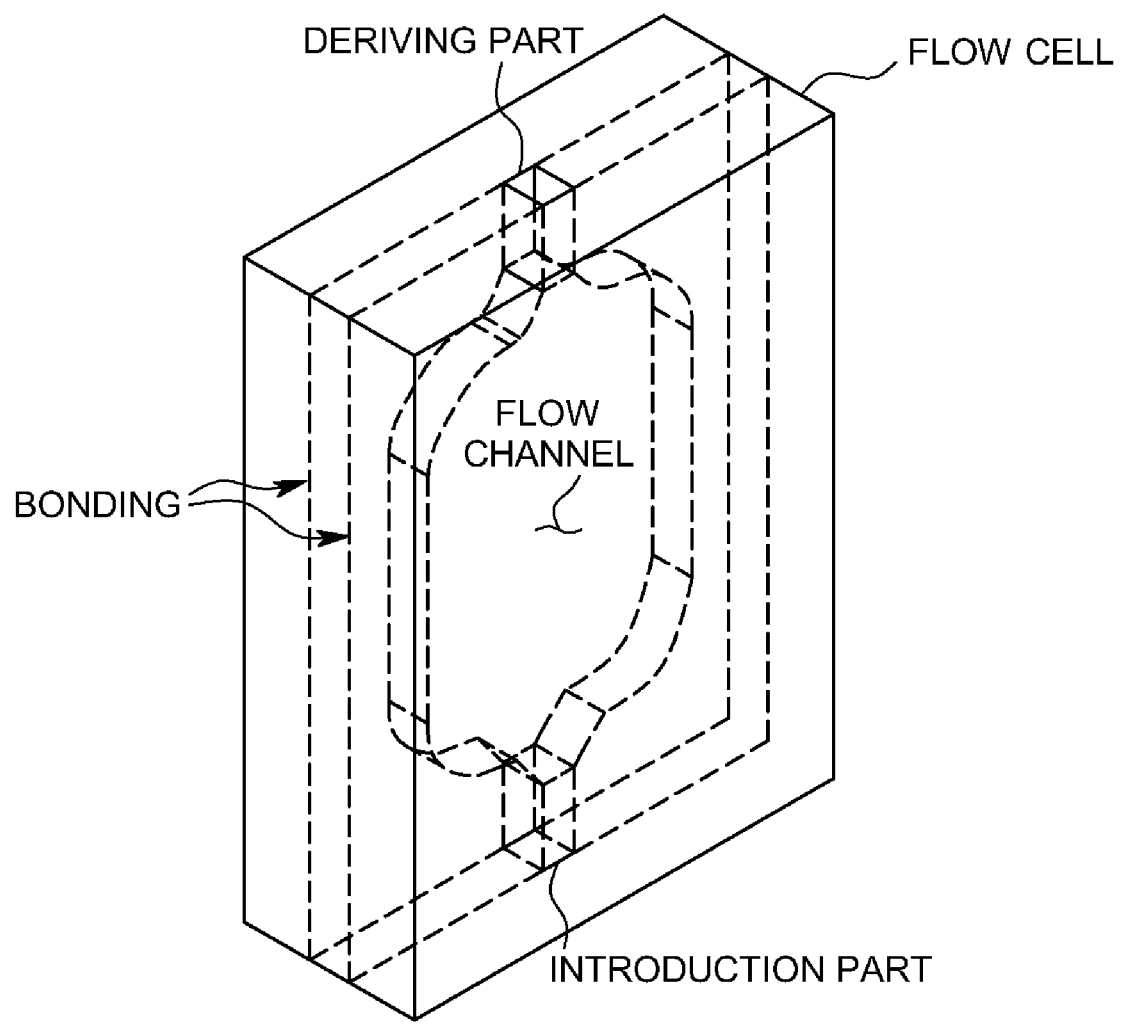
FIG. 10 is a diagram showing a conventional flow cell.

Further, as shown in FIG. 9, the spacer 30 may include a cylindrical holder 90, positioning protrusions 93 each having a shape corresponding to a positioning recess 22 provided on at least one of the end surfaces of the holder 90, length defining members 91 penetrating a peripheral wall of the holder 90 and the positioning protrusions 93 of the holder 90 in the axial direction, and an introduction channel 92 penetrating an opposing position in the outer peripheral surface of the holder 90.

The length of the length defining member 91 is generally equal to a length in the axial direction of a portion where the positioning protrusions 93 are provided in the holder 90. Referring to the materials, the holder 90 is preferably formed of, e.g., PFA (tetrafluoroethylene-perfluoro-alkyl-vinyl-ether copolymer) or PTFE (polytetrafluoroethylene), and the length defining member 91 is preferably formed of sapphire or the like. With these materials, the manufacturing cost can be lower than that of the spacer 30 entirely including sapphire. This specific feature becomes remarkable in the case where the length or thickness of the spacer 30 is increased. Moreover, since the length defining member 91 includes sapphire, which is a material having a low thermal expansion coefficient and high pressure resistance, even though the holder 90 is expanded by heat or configured of a material which cannot withstand the pressing, the distance between the opposing surfaces 20a and 21a of the pair of light transmitting members 20 and 21 can be securely determined.

In addition, although the positioning recess is provided in one of the opposing surfaces of a pair of light transmitting members, it may be provided in both of the opposing surfaces. Further, although the cell is described as a flow cell, a batch cell for use in measurement in a batch processing may be used. Moreover, although the reference cell is provided integrally with a flow channel (sample cell) in which a sample solution flows, it may be separately provided. In addition, the present invention is not limited to the embodiments described above and various changes and modifications thereof can be made within a range unless it departs from the spirit of the present invention. As one example, while the present invention is described above to generally relate to an optical measurement cell for measuring a concentration of a chemical solution such as hydrofluoric acid (HF) in a manufacturing process of, e.g., a semiconductor and the like, it will be appreciated that the optical measurement cell may alternatively be configured to measure not just a concentration per se, but also a measurement that may be used to calculate a concentration, such as a quantity, amount, volume, etc.

It should be understood that the embodiments herein are illustrative and not restrictive, since the scope of the invention is defined by the appended claims rather than by the description preceding them, and all changes that fall within metes and bounds of the claims, or equivalence of such metes and bounds thereof are therefore intended to be embraced by the claims.

REFERENCE CHARACTER LIST

100 . . . Flow cell
10 . . . Flow cell body
11 . . . Accommodating recess
11a . . . Through hole of accommodating recess
13 . . . Solution deriving part
14 . . . Solution introduction part
20 . . . First light transmitting member
21 . . . Second light transmitting member
22 . . . Positioning recess
23 . . . Optical window
30 . . . Spacer
80 . . . Pressing mechanism
90 . . . Holder
L . . . Pipe
102 . . . Semiconductor manufacturing apparatus
104 . . . Light source
106 . . . Photo detecting part
108 . . . Calculating part

The invention claimed is:

1. An optical measurement cell having a pair of optical windows sandwiching a flow channel accommodating a sample solution, comprising:
   a cell body provided with an accommodating recess having a through hole formed in a part of a bottom surface thereof, and a solution introduction part and a solution deriving part which are communicating with an inner circumferential surface of the accommodating recess;
   a pair of light transmitting members accommodated in the accommodating recess and forming the pair of optical windows;
   a spacer contacting respective opposing surfaces of the pair of light transmitting members and defining a distance between the opposing surfaces; and
   a pressing mechanism for pressing the pair of light transmitting members and the spacer toward the bottom surface of the accommodating recess to be brought into close contact with each other so as to form the flow channel connecting to the solution introduction part and the solution deriving part between the pair of light transmitting members,
   wherein a pair of positioning recesses, each having a shape corresponding to the spacer, are provided on at least one opposing surface of the pair of light transmitting members and the spacer is fitted in the positioning recesses so as to be positioned substantially.

2. The optical measurement cell according to claim 1, wherein the positioning recesses are each provided in an outer edge portion of the at least one opposing surface and bottom surfaces of the positioning recesses are formed in a stepwise shape leading to side surfaces of one of the pair of light transmitting members, and
   wherein the spacer is sandwiched between the inner circumferential surface of the accommodating recess and side surfaces of the positioning recesses facing the inner circumferential surface.

3. The optical measurement cell according to claim 1, wherein the positioning recesses are provided on the at least one opposing surface of the pair of light transmitting members arranged in a bottom surface side of the accommodating recess.

4. The optical measurement cell according to claim 1, wherein the accommodating recess has substantially a circular shape in plan view,
   wherein each of the pair of light transmitting members has substantially a circular shape in plan view fitted to the accommodating recess,
   wherein the spacer is a pair of partial arc plates each having a side surface of a partial arc shape of substantially the same circle of the pair of light transmitting members in plan view, and
   wherein the positioning recesses are provided to have a shape substantially the same as the spacer in plan view and are each formed in the outer edge portions of the at least one opposing surface, the positioning recesses sandwiching the solution introduction part and the solution deriving part.

* * * * *